United States Patent [19]

Plessers

[11] 4,362,562

[45] Dec. 7, 1982

[54] METHOD FOR TAKING SAMPLES FROM PIG-IRON MELTS

[75] Inventor: Jacques J. P. Plessers, Helchteren, Belgium

[73] Assignee: Electro-Nite, Philadelphia, Pa.

[21] Appl. No.: 236,087

[22] Filed: Feb. 20, 1981

[30] Foreign Application Priority Data

Feb. 20, 1980 [DE] Fed. Rep. of Germany ....... 3006281

[51] Int. Cl.³ ............................................. G01N 25/02
[52] U.S. Cl. .................................... 75/130 R; 75/53; 374/26
[58] Field of Search .................... 75/53, 130 R; 73/17

[56] References Cited

U.S. PATENT DOCUMENTS

| | | | |
|---|---|---|---|
| 2,980,530 | 4/1961 | Crome | 75/130 R |
| 3,055,756 | 9/1962 | Kanter | 75/130 R |
| 3,072,476 | 1/1963 | Knapp | 75/130 R |
| 3,546,921 | 12/1970 | Bourke | 73/17 |
| 3,565,698 | 2/1971 | de Beaulieu | 75/130 R |
| 3,637,373 | 1/1972 | Bylund | 75/130 R |

*Primary Examiner*—P. D. Rosenberg
*Attorney, Agent, or Firm*—Seidel, Gonda, Goldhammer & Panitch

[57] ABSTRACT

A method of causing a sample of pig iron to solidify to a white structure by adding misch metal to the sampling cavity.

8 Claims, 1 Drawing Figure

METHOD FOR TAKING SAMPLES FROM PIG-IRON MELTS

BACKGROUND

The invention relates to a method of taking samples from pig-iron melts, e.g. from a blast-furnace tapping spout or a normal ladle or a torpedo ladle, the melts solidifying to form a homogeneous white-iron structure, in which the sample solidifies in the sample-taker cavity in the presence of a small quantity of an additive.

There are practical difficulties in taking samples of pig-iron which solidify into a homogeneous white-iron structure (white cast iron). Unless special methods are used, pig-iron solidifies in a structure which has a blackish colour as a result of graphite precipitation. Such samples are unsuitable for complete spectrometric pig-iron analysis, since the samples for analysis must solidify into a white, homogeneous structure which is visible at a fracture face.

In addition, if there are graphite precipitates in the sample, the analysis may not be reproducible and the sample-taking may not be representative; this is particularly important at the end of the heat. Such samples, containing a number of graphite precipitates at the analytical surface, are also unsuitable for quantitative analysis.

Attempts have long been made to control the solidification of pig-iron samples to ensure that they solidify into a homogeneous white-iron structure. One prior-art method is based on the direct conversion of blast-furnace pig-iron into a low-alloy pig-iron at the moment of sampling. In the method, "carbide-forming elements", i.e. chromium and vandium, are added to the sample; their effect is based on the fact that the carbon is bonded, thus preventing the precipitation of graphite, and the sample solidifies into a white-iron structure. The known method has disadvantages in that elements are added and may include the elements under analysis. In addition, the method requires a spoon, in which the added elements are dissolved and mixed with the sample.

French Patent Specification No. 2 171 627 discloses a device for taking pig-iron samples and adapted to solidify the sample into a homogeneous white-iron structure. In the process a given quantity of an additive—pulverulent tellurium—is wrapped in metal foil, e.g. aluminium paper, and placed in the device so that the liquid pig iron dissolves the additive before solidifying.

SUMMARY OF THE INVENTION

The invention, which relates to sample-taking, more particularly of pig-iron, is based on the problem of bringing about solidification to a white-iron structure using an additive which is obtainable under acceptable commercial conditions but also dissolves in the pig-iron quickly enough for the sample to be taken in conventional sample-takers containing a mixing chamber, without additional operations such as the use of a spoon or the like.

It has unexpectedly been found that the samples can be efficiently solidified into a homogeneous white-iron structure if solidification is brought about in the presence of rare earth metals which have an atomic number of 57–72 in Group III of the periodic table. According to the invention, the preformed rare earth metal is added in the form of commercial misch metal.

According to another feature of the invention, the additives are added in the proportion of about 0.3 to 6 wt. % of the sample.

The drawing is a photomicrograph with a magnification of 10 and shows at the top half the results of this invention and at the bottom half a sample which was not treated in accordance with this invention.

DETAILED DESCRIPTION

The sample can be taken e.g. by a known device having a mixing-chamber which can be placed on the end of a cardboard tube. The device comprises a sand member having a cavity in which the sample-container is disposed in order to draw a disc or plate-shaped sample. The inlet opening is prolonged by a tube to the top end of the sand member, on which an inverted metal cap is placed, the cavity in the cap surrounding the supply opening. The upturned bottom of the cup-shaped cap is formed with an opening. A second, similarly constructed cap is placed over the first cap and its bottom is likewise perforated. The two openings in the cap bottoms are offset from one another and from the opening of the tube. The cavities formed by the caps are "mixing chambers". The top cap is then covered by a slag cap, which is covered by a protective cardboard cap.

In order to withdraw a sample of pig-iron containing 4.5% carbon, 0.9% silicon and 0.02% phosphorus, a misch metal wire helix 75 mm long and 2.2 mm in diameter was placed in the top mixing-chamber, i.e. in the chamber between the two perforated bottoms of the lower caps. The wire weighed about 2 g. The sample-taker was placed on the end of a cardboard measuring-lance and the sample was drawn by immersion in the pig-iron melt.

After cooling, the sample was removed from the sample-container and broken. As the top half of the accompanying drawing shows, it solidified into a white-iron structure.

The same test was repeated, using an identical device without adding misch metal. The fracture face is shown in the lower half of the drawing and shows considerable, clearly recognizable, graphite precipitation (grey solidification).

The present invention may be embodied in other specific forms without departing from the spirit or essential attributes thereof and, accordingly, reference should be made to the appended claims, rather than to the foregoing specification, as indicating the scope of the invention.

I claim:

1. A method of preparing a molten pig-iron sample for spectrometric analysis comprising:
    inserting a sample-taking means into a pig-iron melt, said sample-taking means containing a quantity of misch metal;
    removing said sample-taking means;
    solidifying said molten pig-iron sample; and
    analyzing said solidified sample.

2. A method in accordance with claim 1 wherein the quantity of misch metal is between about 0.3 and about 6.0 weight percent.

3. A method in accordance with claim 1 wherein the sample-taking means is a ladle.

4. A method in accordance with claim 1 wherein the sample-taking means is a tapping spout.

5. A method in accordance with claim 1 wherein the sample-taking means is a chamber means mounted on a lance.

6. A method in accordance with claim 5 including:
providing a sand member having a mixing chamber containing said misch metal;
providing an inlet opening at the bottom of said sand member;
providing a tube means communicating said inlet opening with said mixing chamber;
using first and second metal caps to form the upper and lower boundaries of said mixing chamber, said first and second metal caps each having an aperture therethrough.

7. A method in accordance with claim 6 wherein said apertures in said first and second metal caps are offset from one another and said inlet opening.

8. A method in accordance with claim 6 wherein said second metal cap is covered by a slag cap, which is in turn covered by a protective cardboard cap.

* * * * *